United States Patent [19]

Elattar

[11] Patent Number: 5,061,672

[45] Date of Patent: Oct. 29, 1991

[54] ACTIVE MASS FOR MAKING ORGANOHALOSILANES

[75] Inventor: Azza A. Elattar, Niagara Falls, N.Y.

[73] Assignee: Elkem Metals Company, Pittsburgh, Pa.

[21] Appl. No.: 472,095

[22] Filed: Jan. 30, 1990

[51] Int. Cl.$^5$ .............. B01J 21/06; B01J 23/80; B01J 27/182; B01J 37/22

[52] U.S. Cl. .................. 502/244; 502/214; 502/241; 502/242

[58] Field of Search ............ 502/244, 345, 241, 242, 502/214; 556/472

[56] References Cited

U.S. PATENT DOCUMENTS

| | | | |
|---|---|---|---|
| 2,380,995 | 8/1945 | Rochow | 556/476 |
| 2,380,996 | 8/1945 | Rochow | 556/476 |
| 2,380,997 | 8/1945 | Rochow | 556/476 |
| 2,389,931 | 11/1945 | Reed et al. | 260/607 |
| 2,427,605 | 9/1947 | Hurd | 502/244 |
| 2,464,033 | 3/1949 | Gilliam | 260/448.2 |
| 2,887,502 | 5/1959 | Bluestein | 260/448.2 |
| 2,903,473 | 9/1959 | Takami et al. | 260/448.2 |
| 3,069,452 | 12/1962 | Rossmy | 260/448.2 |
| 3,133,109 | 5/1964 | Dotson | 260/448.2 |
| 3,555,064 | 1/1971 | Turetskaya et al. | 260/448.2 |
| 4,314,908 | 2/1982 | Downing et al. | 502/244 |
| 4,500,724 | 2/9185 | Ward et al. | 556/472 |
| 4,503,165 | 3/1985 | Hashiguchi et al. | 502/225 |
| 4,504,597 | 3/1985 | Klar et al. | 502/225 |
| 4,520,130 | 5/1985 | Hashiguchi | 502/345 |
| 4,578,494 | 3/1986 | Marko et al. | 556/452 |
| 4,645,851 | 2/1987 | Prud'Homme | 556/472 |
| 4,661,613 | 4/1987 | Prud'Homme et al. | 502/244 |
| 4,824,984 | 4/1989 | Klar et al. | 502/345 |
| 4,864,044 | 9/1989 | Lewis et al. | 502/345 |

FOREIGN PATENT DOCUMENTS

| | | | |
|---|---|---|---|
| 3100014 | 5/1988 | Japan | 502/345 |
| 3107808 | 5/1988 | Japan | 502/345 |

*Primary Examiner*—Carl F. Dees
*Attorney, Agent, or Firm*—Lucas & Just

[57] ABSTRACT

The active mass is produced by first forming a contact mass of particulate silicon metal and particulate copper catalyst and then heating the contact mass at a temperature of between 250°–335° C. in the presence of methylchloride to form the active mass. Zinc can be added to the contact mass.

10 Claims, No Drawings

ACTIVE MASS FOR MAKING ORGANOHALOSILANES

This invention relates to production of organohalosilanes such as dimethyldichlorosilane and, more specifically, to a process for forming an active mass and the active mass produced by the process.

Typically, organohalosilanes are made in a copper-catalyzed exothermic reaction between silicon and a gaseous organohalide, like methylchloride, at a temperature of 300° C. Such a process was first discovered in the 1940's by E.G. Rochow and his co-worker and has since been named the Rochow direct process. See U.S. Pat. No. 2,380,995 issued Aug. 7, 1945.

In order to have an efficient reaction between the silicon and the organohalide, a copper catalyst is used. Prior art has described alloying silicon metal with the copper catalyst in a sintering process wherein a mixture of particulate silicon and particulate copper catalyst is heated to a temperature of about 1000° C. in a reducing atmosphere for a period of time sufficiently long to form an alloy of copper and silicon. See U.S. Pat. No. 2,380,996 issued Aug. 7, 1945. The particulate mix is referred to as a contact mass and the alloyed mass as an active mass.

Improvements in the process for making organohalosilanes have primarily focused on the use of additional components with the silicon metal for increasing the efficiency of the overall reaction between the silicon metal and the organohalide. For instance, U.S. Pat. No. 2,427,605 issued Sept. 16, 1947 teaches forming a contact mass with the addition of zinc or aluminum to the silicon metal and copper catalyst. U.S. Pat. No. 2,464,033 issued Mar. 8, 1949 teaches the addition of zinc or zinc halide as a promoter; U.S. Pat. No. 4,500,724 issued Feb. 19, 1985 teaches using tin along with zinc and copper at certain critical weights; U.S. Pat. No. 4,645,851 issued Feb. 24, 1987 teaches forming a solid contact mass of silicon, copper catalyst, and adding tin, antimony, or mixtures thereof and barium and strontium or compounds thereof, a zinc promoter is preferably included in the contact mass; U.S. Pat. No. 4,824,984 issued Apr. 25, 1989 teaches using zinc from specific sources with the copper catalyst.

Improvements to the production of organohalosilane have also been suggested in the type of copper catalyst used in the reaction. See U.S. Pat. Nos. 4,503,165 issued Mar. 5, 1985; 4,504,597 issued Mar. 12, 1985; and 4,520,130 issued May 28, 1985.

The contact mass, when brought into contact with an organohalide, will not react to form the organohalosilane monomer until it has been transformed into an active mass.

There are a number of ways to form a stable active mass. One way is to heat the silicon and copper catalyst in a reducing atmosphere to a temperature of about 1000° C. A similar technique is taught in U.S. Pat. No. 4,314,908 issued Feb. 9, 1982. Patent '908 teaches that an active mass having spots of copper-silicon alloy substantially uniformly distributed on the surface of the silicon particle is made by blending the copper catalyst and silicon metal and then heating the blend in a reducing atmosphere at a temperature above the melting point of the copper-silicon alloy, i.e., 960° C., but below the melting point of copper, i.e., 1080° C., to avoid sintering the metallic particles.

One of the major drawbacks of these processes is that they require an exceedingly high temperature to transform the contact mass into an active mass.

It has now been discovered that a stable copper-catalyzed silicon active mass for production of organohalosilanes can be made at substantially lower temperatures than heretofore known. The active mass of the present invention is made by forming a contact mass comprising particles of silicon metal and a catalytically effective amount of a particulate copper catalyst and heating said contact mass in the presence of an organohalide gas at a temperature of between about 250° C. and 335° C. for a period of time which is sufficiently long to form active spots of copper-silicon alloy on the surface of the silicon metal and sufficiently short to prevent the formation of an organohalosilane. Active spots of silicon-copper alloy are alloys of metallic copper and silicon which, when brought into contact with an organohalide gas in the presence of particulate silicon metal at about 305° C., produce organohalosilanes. It has been found that the heating step is shorter at 335° C. than at 250° C.; it takes about 4 hours at 250° C. and about 15 minutes at 335° C. Preferably, the heating step is conducted for about one-quarter hour to about 5 hours at a temperature between about 250° C. to about 335° C. The preferred organohalide gas is methylchloride.

A stable active mass product is cooled to room temperature after the heating step. The product of the process has been found to have a good shelf life, e.g., in excess of 4 months.

The advantages associated with the present invention are numerous. For example, methylchloride is less hazardous than hydrogen gas which has been used to create a reducing atmosphere at high temperatures for formation of an active mass. In addition, the temperatures employed in the present invention (250-335° C.) are much milder than those in the high temperature processes (1000° C.). Further, any kind of promoter (especially the volatile ones) can be used in the process.

The active mass of the present invention, when brought in contact with an organohalide at about 300° C., will start to produce organohalosilanes without any induction period.

A contact mass is formed by blending particulate silicon metal and copper catalyst. A promoter can be added.

The particulate silicon metal is preferably a silicon metal having a purity of about 95% by weight or above silicon, more preferably, it will contain greater than 98% by weight silicon. The amount of silicon metal in the contact mass is preferably about 90% to about 99% by weight based on the total weight of the contact mass. More preferably, the contact mass contains about 95% to about 99% by weight silicon metal.

The copper catalyst in a particulate form such as copper or a copper compound is used. Suitable copper catalysts include copper; copper oxides, $Cu_2O$, $CuO$; copper formate; and copper chloride. Mixtures of metallic copper and copper oxides work well. The amount of copper catalyst present in the contact mass is preferably about 0.2 to 10% by weight based on the total weight of the contact mass. The amount of catalyst is such that preferably the amount of the copper in the contact mass is about 0.5 to about 5% by weight based on the weight of the contact mass.

Promoters in a particulate form such as zinc compounds like zinc, zinc carbonate, zinc formate, zinc acetate; tin and tin compounds; phosphorus and phosphorus compounds; antimony and antimony compounds; manganese and manganese compounds; titanium and titanium compounds; and aluminum and aluminum compounds; and mixtures thereof can be added to the contact mass. The preferred promoter is zinc. The amount of promoter present in the contact mass is preferably about 0.005 to about 2.5% by weight based on the weight of the contact mass; or about 0.01% to 0.5% based on the weight of the copper catalyst. The promoter can be introduced into the contact mass as a component of the copper catalyst.

The contact mass should be in particulate form and preferably range between about 0.1 to 800 microns and, more preferably, about 0.1 to 150 microns in size. The particle size is dictated by the type of reactor used for the production of the organohalide silicon. Typically, a fluidized bed, a stirred bed or a fixed bed reactor is used.

The step of heating the contact mass in the presence of an organohalide is carried out at a temperature between about 250° C. and 335° C. More preferably, the temperature of the conversion is between about 260° C. and about 335° C. Good results have been obtained at temperatures of about 310° C. to 330° C.

Suitable organic halides include methylchloride, ethylchloride, n-propylchloride, isopropylchloride and vinylchloride. Preferably, methylchloride is used.

The heating step is conducted at atmospheric pressure. However, higher pressures can be used.

The heating takes place in a reactor. Fixed bed, moving bed, stirred bed and fluid bed reactors can be used.

The time for the reaction is about ¼ hour to about 5 hours. Good results have been obtained in 2 hours. The length of time for the reaction depends on the composition of the contact mass. The reaction should proceed to a point just prior to the production of the organohalosilane. The heating time should be sufficiently long to produce an active mass and yet produce substantially no organohalosilane.

These and other aspects of the present invention may be more completely understood by reference to the following examples:

EXAMPLE 1

This example illustrates preparation of an active mass in accordance with the present invention and that no carbon deposition took place during the active mass formation. Carbon formed in the reactor during the transformation of the contact mass to the active mass reduces the bed life of the reactor.

A contact mass was prepared by blending 200 parts by weight of silicon particles (70×140 mesh), 9 parts by weight of a copper catalyst (containing 16.9% metallic copper, 45.5% $Cu_2O$ and 36.9% CuO), and 1.2 parts by weight of zinc carbonate together in a blender. The contact mass was divided in two portions denoted as 1 and 2 in Table 1 below. Both masses were subjected to a heating step at different temperatures. The heating step took place in a fixed bed laboratory stainless steel tube reactor under methylchloride at a constant mass flow rate of about 0.33 standard liter per minute. The methylchloride and any methylchlorosilanes produced from the reaction were analyzed by gas chromatography. Formation of the active mass was identified by detecting methylchlorosilanes in the methylchloride stream. About 3% of the silicon was consumed in the active mass production. After forming the activated mass, methylchloride flow was terminated and replaced with nitrogen gas while the reactor was cooling down to ambient temperature. The amount of carbon in the produced active mass and in the initial unreacted contact mass was determined. The results are compared in Table 1 below.

TABLE 1

| Sample | Heating Step Temp °C. | Time (hr.) | Carbon % Wt. |
|---|---|---|---|
| Contact mass | — | — | 0.185 |
| Active mass (1) | 310 | 3.0 | 0.140 |
| Active mass (2) | 330 | 2.5 | 0.150 |

The results showed that no carbon deposition took place during the production of the activated mass, i.e., methylchloride did not crack under the utilized conditions.

EXAMPLE 2

This example illustrates the shelf life of the active mass of the present invention.

The procedure and equipment used were the same as those described in Example 1. The active mass (AM) was formed from a contact mass formed in accordance with Example 1 at 330° C. and stored at ambient temperature for 4 months. The performance of the AM was evaluated for Rochow direct process in a fluidized bed reactor operating at 305° C. with a flow rate of 0.55 l/min. methylchloride and one atmospheric pressure. The production rate of crude silanes (g/hr.); percentage of dimethyl-dichlorosilane in crude silanes (% D) and percentage of silicon converted to crude silanes in a 24 hour run (% Si conv.) were measured. Comparison between the performance of the 4 month old AM and the freshly prepared AM is listed in Table 2.

TABLE 2

| AM Sample | Average performance in a 24 hour run | | |
|---|---|---|---|
| | Crude silanes g/hr | % D (Me2SiCl2) | Total % Si Conv. 24 Hrs. |
| (3) Fresh | 10.1 | 90.2 | 28.6 |
| (3) 4 mo. old | 10.2 | 89.7 | 29.2 |

The above results showed that the active mass retained its reactivity for at least four months, in that similar results were obtained with the old and with the fresh active mass.

EXAMPLE 3

This example illustrates that an active mass can be formed without consuming silicon.

The procedure and equipment used were the same as those described in Example 1 except that the active mass was formed by treating the contact mass with methylchloride at 330° C. without any methylchlorosilane production, i.e., no loss in the silicon charge; silicon recovery was 99.9%. The methylchloride was terminated before formation of any methylchlorosilanes. The produced active mass was stored for 70 days, Sample 5, and its performance was determined and compared with a 20 hour old active mass, Sample 4, prepared with 3% silicon consumption. The results obtained are listed in Table 3 below.

TABLE 3

| AM Sample | Average performance in a 24 hour run | | |
|---|---|---|---|
| | Crude silanes g/hr. | % (D) | % Si Conv. |
| 4* | 9.3 | 86.8 | 25.8 |

TABLE 3-continued

| | Average performance in a 24 hour run | | |
|---|---|---|---|
| AM Sample | Crude silanes g/hr. | % (D) | % Si Conv. |
| 5** | 11.0 | 86.0 | 26.7 |

*Active mass was 20 hours old. 3% of silicon was consumed in the active mass formation.
**Active mass was 70 days old. No silicon was consumed in the active mass formation.

The above results demonstrate that the active mass can be formed without loss in the charged silicon. Also, it has ability to retain its reactivity for at least 70 days.

EXAMPLE 4

This example compares an active mass made in accordance with the present invention versus the results reported for an active mass prepared in accordance with U.S. Pat. No. 4,314,908. The contact mass for this test was prepared in accordance with Example 1, except that catalyst charge was 4 parts by weight, i.e. 2%. While equipment limitations prevented a direct comparison, it is possible to extrapolate performance of the present invention to compare it with that reported in the '908 patent. The results obtained are summarized in Table 4 below.

TABLE 4

| Evaluation Conditions | Prior Art Active mass (H2 @ 1000C Plus HCl gas @ 350C) | Present Invention Active mass (Me₃Cl @ 330C) | |
|---|---|---|---|
| Reaction Temperature, C | 320 | 305 | 320** |
| Reaction Pressure, atm | 4 | 1 | 4 |
| Catalyst Concentration, % | 2.7 | 2 | 2 |
| T/D* | .071 | .086 | <.086 |
| G/hr., Product (Silane) | 31.1 | 7.2 | >42 |
| Zinc added during the Reaction | Yes | No | No |

*Trimethyltrichlorosilane/dimethyldichlorosilane by weight
**Extrapolated performance of the present invention at 4 atmosphere and 320° C.

It is clear that the active mass of the present invention is superior to the active mass of the prior art.

It will be understood that it is intended to cover all changes and modifications of the preferred embodiments herein chosen for the purpose of illustration which do not constitute a departure from the spirit and scope of the invention.

What is claimed is:

1. A process for making a copper-catalyzed silicon active mass for production of organohalosilanes comprising the steps of:
   (a) forming a contact mass comprising particulate silicon metal, and a catalytically effective amount of a particulate copper catalyst;
   (b) heating said contact mass in the presence of an organohalide gas only at a temperature of between about 250° C. and 335° C. for a period of time sufficient to form active spots of copper-silicon alloy on the surface of the silicon metal without producing any substantial quantity of an organohalosilane; and
   (c) cooling said contact mass with active spots of copper-silicon alloy on the surface of the silicon metal to room temperature thereby forming a stable, active mass for use in the production of organohalosilanes.

2. The process of claim 1 wherein the organohalide is methylchloride.

3. The process of claim 1 wherein the contact mass comprises about 90 parts to about 98 parts by weight of said silicon metal based on the total weight of said contact mass, said silicon metal having a purity of about 95% or above; and about 0.2 parts to about 10 parts by weight of said copper catalyst based on the total weight of said contact mass.

4. The process of claim 1 further comprising the addition of a zinc promoter to said contact mass.

5. The process of claim 1 wherein the heating step is conducted for about ¼ hour to about 5 hours.

6. The process of claim 1 wherein the temperature during said heating step is between about 310° C. and about 330° C.

7. The product of the process of claim 11.

8. An active mass made by a process comprising:
   (a) forming a contact mass comprising about 90 to 98% by weight particulate silicon; about 0.2 to 10% by weight particulate copper catalyst, said copper catalyst selected from the group consisting of copper, copper oxide, copper chloride, copper formate, and mixtures thereof, and about 0.005 to 2.5% by weight of a promoter, said promoter selected from the group consisting of zinc, zinc carbonate, zinc formate, zinc acetate, tin and tin compounds, phosphorus and phosphorus compounds, antimony and antimony compounds, manganese and manganese compounds, titanium and titanium compounds, aluminum and aluminum compounds, and mixtures thereof;
   (b) heating said contact mass in the presence of an organohalide gas only at a temperature between about 250° and 335° C. for a period of time sufficient to form active spots of copper-silicon alloy on the surface of the silicon metal without producing any substantial quantity of an organohalosilane; and
   (c) cooling said contact mass with active spots of copper-silicon alloy on the surface of the silicon metal to room temperature thereby forming a stable, active mass for use in the production of organohalosilanes.

9. The active mass of claim 8 wherein the particulate silicon is at least 95% pure silicon.

10. The active mass of claim 8 wherein the particulate silicon is at least 98% pure silicon.

* * * * *

UNITED STATES PATENT AND TRADEMARK OFFICE
CERTIFICATE OF CORRECTION

PATENT NO. : 5,061,672
DATED : October 29, 1991
INVENTOR(S) : Azza A. Elattar

It is certified that error appears in the above-identified patent and that said Letters Patent is hereby corrected as shown below:

Column 6, line 26, change the dependency from "claim 11" to --claim 1--.

Signed and Sealed this

Ninth Day of March, 1993

*Attest:*

STEPHEN G. KUNIN

*Attesting Officer*  Acting Commissioner of Patents and Trademarks